United States Patent
Fournier

(10) Patent No.: US 10,512,678 B2
(45) Date of Patent: *Dec. 24, 2019

(54) ENZYME FORMULATION FOR REDUCING HISTAMINE INTOLERANCE

(71) Applicant: Thea Fournier, North Andover, MA (US)

(72) Inventor: Thea Fournier, North Andover, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/853,771

(22) Filed: Dec. 23, 2017

(65) Prior Publication Data

US 2018/0117130 A1    May 3, 2018

Related U.S. Application Data

(63) Continuation-in-part of application No. 15/079,404, filed on Mar. 24, 2016, now Pat. No. 9,849,164.

(51) Int. Cl.
*A61P 25/24* (2006.01)
*A61K 9/48* (2006.01)
*A61P 17/00* (2006.01)
*A61K 38/54* (2006.01)

(52) U.S. Cl.
CPC ............ *A61K 38/54* (2013.01); *A61K 9/4816* (2013.01); *A61P 17/00* (2018.01); *A61P 25/24* (2018.01); *C12Y 302/01001* (2013.01); *C12Y 302/01022* (2013.01); *C12Y 302/01108* (2013.01); *C12Y 303/01* (2013.01); *C12Y 304/14005* (2013.01); *C12Y 402/02002* (2013.01)

(58) Field of Classification Search
CPC ............ A61K 38/54; C12Y 302/01108; C12Y 303/01; C12Y 402/02002; C12Y 302/01001; C12Y 302/01022; C12Y 304/14005; A61P 17/00
See application file for complete search history.

(56) References Cited

PUBLICATIONS

Wolfson et al., Technical Summary "Making Sense of Digestive enzymes", Klaire Labs, 2008, p. 1-8.*
Maintz and Novak, Am J Clin Nutr, 2007, vol. 85, p. 1185-1196.*
Ku et al. Capsugel, Performance Qualification of a New Hypromellose Capsule, 2011, p. 1-15 +1*

* cited by examiner

*Primary Examiner* — Kade Ariani
(74) *Attorney, Agent, or Firm* — Eric P. Mirabel, JD, LLM

(57) ABSTRACT

Disclosed is a formulation of the following enzymes: Alpha-galactosidase, Alpha amylase, Beta Glucanase, Lactase, BioCor DPP=IV (Proprietary blend) and Pectinase, which has been found to be effective in treating histamine intolerant people, and causing a significant improvement in a wide variety of pathologies and symptoms, including, but not limited to: inflammation, pruritus, urticaria, hypotension, tachycardia, fatigue, migraines, conjunctivitis, incontinence, nasal congestion, panic attacks, acid reflux, depression and angioedema.

10 Claims, No Drawings

ENZYME FORMULATION FOR REDUCING HISTAMINE INTOLERANCE

RELATED APPLICATIONS

This application is a CIP of Ser. No. 15/079,404, filed Mar. 24, 2016.

BACKGROUND

In the past six years or so, there has been an increase in research about histamine intolerance, which has generated clinical evidence of it, and more internet sites with options to help those who are intolerant. It is believed that many who are intolerant to histamine can have the intolerance traced to genetically engineered foods ("GMO foods") that have created a disturbance of the "gut biome," or intestinal bacteria, damaging gut health. In susceptible individuals, these changes in the gut biome create a condition called "histamine intolerance." This has also contributed to deficiencies in the body's histamine breakdown process, which involve the DAO enzyme and the N-methyltransferase (HMT) enzyme. These susceptible individuals, who cannot efficiently break down histamine, react to the excessive accumulation of histamine in their bodies.

There are many sources that increase histamine in the body which include, but are not limited to: (1) Foods that naturally contain this chemical compound, including, but not limited to: fermented foods, yogurt, kefir, citrus fruits, most berries, dried fruits, tomatoes, spinach, chocolate, vinegar, and eggs; (2) Some foods, like nuts and seeds, though containing no histamine, can trigger a release of histamine in the body; (3) Leftovers (The longer food is stored, the greater its histamine content); (4) An over-growth of certain bacteria in the GI tract, which can produce an excess of histamine; (5) Certain strains of probiotics, and (6) Stress.

Over the past ten years, the inventor found that by reducing histamine intake in the body through daily appropriate dietary choices, though challenging and often problematic, appears to be highly effective in treating a wide range of histamine-related symptoms and conditions, including, but not limited to: inflammation, pruritus, urticaria, hypotension, tachycardia, fatigue, migraines, conjunctivitis, incontinence, nasal congestion, panic attacks, acid reflux, depression and angioedema. The invention herein relates to a novel formulation for treatment and prevention of histamine-related conditions.

SUMMARY

A formulation of the following enzymes: Alpha-galactosidase, Alpha amylase, Beta Glucanase, Lactase, BioCor DPP-IV (National Enzyme Company, Inc., Forsyth, Missouri), and Pectinase (the "Formulation"), has been found to be effective in treating histamine intolerant people, or preventing symptoms, and causing a significant improvement in a wide variety of symptoms/conditions, including, but not limited to: inflammation, pruritus, urticaria, hypotension, tachycardia, fatigue, migraines, conjunctivitis, incontinence, nasal congestion, panic attacks, acid reflux, depression and angioedema. It is believed that the Formulation helps to rebalance the "gut biome" and to help restore deficiencies of an impaired liver pathway that support the body's overall histamine breakdown process, thereby reducing the accumulation of histamine in the body.

More particularly, the preferred dosages of the enzymes in the Formulation are as follows: Alpha-galactosidase: 80 GaLU; Alpha amylase: 150 DU; Beta Glucanase: 70 BGU; Lactase: 1,000 ALU; BioCor DPP-IV Proprietary blend, 80 mg, and Pectinase: 17 ENDO-PGU. The preferred dosing is ingesting two or more capsules of the Formulation with the foregoing contents with each meal. A preferred carrier for the Formulation is a vegetable capsule (including, mostly cellulose and distilled water). The Formulation should be free of any of the following: milk/casein, gluten, dairy, egg, soy, corn, peanuts, tree nuts, fish and shellfish, and should not contain any artificial colors, flavors or preservatives.

The preferred dosages and dosing regime for the formulation, are not the only dosages possible, and other more optimal dosages and dosing regimes may be discovered with routine experimentation, now that the preferred dosages are known. The routine experimentation would involve providing different dosages under different regimes, using behavioral kinesiology to determine the appropriate dosage and optimal regime for each individual child or adult in the case study, and determining which patients improved most in their monitored symptoms and conditions.

The starting point, for determining optimal dosing and an optimal regime, is the preferred dosages, administered at mealtimes, as above. Variations could be doubling, halving, or otherwise and reducing the quantities of one or more of the enzymes in a formulation. The dosing regime modifications could include increasing or reducing the number of administrations of the formulation each day for patients in a particular group. Such experimentation is routine in the pharmaceutical industry.

A discussion of testing and demonstrating the safety and efficacy of the formulation is set forth below in the Detailed Description.

DETAILED DESCRIPTIONS

The treatment and prevention regime with the formulation of the invention will now be described in greater detail with reference to the example below of an administration regime and testing with a number of patients.

EXAMPLE

Administering the Formulation to Screened Patients 20 participants intolerant of histamines were identified with muscle testing, a self-reported questionnaire with 320 symptoms indicative of the condition, and together with participant's history and a participant examination. These patients presented a variety of symptoms, including, but not limited to one or more of: pruritus, urticaria, hypotension, tachycardia, fatigue, conjunctivitis, incontinence, nasal congestion, panic attacks, acid reflux, depression and angioedema. During the initial phase, all the participants initially ate a low histamine diet for three or more months. During this phase, participant's symptoms were monitored at monthly visits. Many participants experienced some improvement in their symptoms during this phase; but symptomology persisted for the majority, because histamine intolerance is cumulative, i.e., it is not always immediate and is difficult to mitigate.

The Theazyme-H formulation was administered to each patient at least twice per day. Theazyme-H has the active ingredients: Alpha-galactosidase, 80 GaLU; Alpha amylase, 150 DU; Beta Glucanase, 70 BGU; Lactase, 1,000 ALU; (BioCor) DPP-IV, 80 mg and Pectinase, 17 ENDO-PGU.

Participant's symptoms were monitored monthly and after three months or more on the formulation (the "Active Phase"), a follow-up questionnaire was administered to determine if their symptoms had improved or been resolved and if their histamine intolerance had been reduced.

Among the indications monitored at the end of the Active Phase for all participants were urticaria and depression—which are associated with histamine intolerance. The results for these indications were as follows:

Urticaria: Seven participants initially indicated urticaria, but following the Active Phase, two reported marked improvement in urticaria episodes and four participants reported no urticaria episodes during the Active Phase. One participant had no noticeable improvement;

Depression: Eight participants initially indicated depression, and at the end of the Active Phase, four reported marked improvement in depression during the Active Phase, and three reported no depression episodes during the Active Phase. One participant had no noticeable improvement.

Similar positive results in a number of patients were also shown in this study for pruritis, panic attacks, angioedema, fatigue and nasal congestion. These positive results were submitted during prosecution of U.S. Ser. No. 15/079,404 (Allowed).

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A method of treating, preventing or ameliorating histamine intolerances symptoms, the method comprising administering to a subject in need a formulation comprising active ingredients Alpha-galactosidase, Alpha amylase, Beta Glucanase, Lactase, DPP-IV and Pectinase, thereby treating, preventing or ameliorating said one or more histamine related symptoms.

2. The method of claim 1 wherein the active ingredients in the formulation have the following quantities: Alpha-galactosidase: 80 GaLU; Alpha amylase, 150 DU; Beta Glucanase, 70 BGU; Lactase, 1,000 ALU; DPP-IV, 80 mg, and Pectinase: 17ENDO-PGU.

3. The method of claim 2 wherein the active ingredients are administered to the subject at twice the quantities therein with each meal consumed.

4. The method of claim 1 wherein the formulation is encapsulated in a vegetable capsule comprising cellulose and distilled water.

5. The method of claim 4 wherein the formulation does not contain any of the following: milk, casein, gluten, dairy, egg, soy, corn, peanuts, tree nuts, fish, shellfish, and, artificial colors, flavors or preservatives.

6. A method of treating, preventing or ameliorating urticaria or depression associated with histamine intolerance, the method comprising administering to a subject in need a formulation comprising active ingredients: Alpha-galactosidase, Alpha amylase, Beta Glucanase, Lactase, DPP-IV and Pectinase, thereby treating, preventing or ameliorating said urticaria or depression associated with histamine intolerance.

7. The method of claim 6 wherein the active ingredients in the formulation have the following quantities: Alpha-galactosidase: 80 GaLU; Alpha amylase, 150 DU; Beta Glucanase, 70 BGU; Lactase, 1,000 ALU; DPP-IV, 80 mg, and Pectinase: 17ENDO-PGU.

8. The method of claim 7 wherein the active ingredients are administered to the subject at twice the quantities therein with each meal consumed.

9. The method of claim 6 wherein the formulation is encapsulated in a vegetable capsule comprising cellulose and distilled water.

10. The method of claim 9 wherein the formulation does not contain any of the following: milk, casein, gluten, dairy, egg, soy, corn, peanuts, tree nuts, fish, shellfish, and, artificial colors, flavors or preservatives.

* * * * *